(12) United States Patent
Terry et al.

(10) Patent No.: US 9,993,498 B2
(45) Date of Patent: Jun. 12, 2018

(54) METHOD FOR THE PREVENTION AND TREATMENT OF GASTROINTESTINAL DISTRESS IN HORSES AND OTHER SPECIES

(71) Applicant: Kaeco Group, Inc., Savannah, MO (US)

(72) Inventors: Kelly Terry, Savannah, MO (US); Leon Kratochvil, Savannah, MO (US); James Harless, Papillion, NE (US); Tom Kratochvil, Arlington, NE (US)

(73) Assignee: Kaeco Group, Inc., Savannah, MO (US)

( * ) Notice: Subject to any disclaimer, the term of this patent is extended or adjusted under 35 U.S.C. 154(b) by 0 days. days.

(21) Appl. No.: 15/388,425

(22) Filed: Dec. 22, 2016

(65) Prior Publication Data

US 2017/0333471 A1 Nov. 23, 2017

Related U.S. Application Data

(62) Division of application No. 15/161,689, filed on May 23, 2016, now Pat. No. 9,694,042.

(51) Int. Cl.

| | | |
|---|---|---|
| *A61K 31/736* | (2006.01) | |
| *A61K 9/00* | (2006.01) | |
| *A61K 31/685* | (2006.01) | |
| *A61K 31/714* | (2006.01) | |
| *A61K 31/702* | (2006.01) | |
| *A61K 9/14* | (2006.01) | |
| *A61K 35/747* | (2015.01) | |
| *A61K 35/744* | (2015.01) | |
| *A61K 31/455* | (2006.01) | |
| *A61K 31/51* | (2006.01) | |
| *A61K 31/525* | (2006.01) | |
| *A61K 31/4415* | (2006.01) | |
| *A61K 31/4188* | (2006.01) | |
| *A61K 31/352* | (2006.01) | |
| *A23K 50/20* | (2016.01) | |
| *A23K 20/158* | (2016.01) | |
| *A23K 10/18* | (2016.01) | |
| *A23K 20/174* | (2016.01) | |
| *A23K 20/20* | (2016.01) | |
| *A23K 10/30* | (2016.01) | |
| *A23K 20/10* | (2016.01) | |

(52) U.S. Cl.
CPC ............ *A61K 31/736* (2013.01); *A23K 10/18* (2016.05); *A23K 10/30* (2016.05); *A23K 20/10* (2016.05); *A23K 20/158* (2016.05); *A23K 20/174* (2016.05); *A23K 20/20* (2016.05); *A23K 50/20* (2016.05); *A61K 9/0053* (2013.01); *A61K 9/14* (2013.01); *A61K 31/352* (2013.01); *A61K 31/4188* (2013.01); *A61K 31/4415* (2013.01); *A61K 31/455* (2013.01); *A61K 31/51* (2013.01); *A61K 31/525* (2013.01); *A61K 31/685* (2013.01); *A61K 31/702* (2013.01); *A61K 31/714* (2013.01); *A61K 35/744* (2013.01); *A61K 35/747* (2013.01); *A23Y 2220/03* (2013.01); *A23Y 2220/17* (2013.01); *A23Y 2220/67* (2013.01)

(58) Field of Classification Search
CPC combination set(s) only.
See application file for complete search history.

(56) References Cited

U.S. PATENT DOCUMENTS

| 7,824,706 | B2 * | 11/2010 | Bedding | ............... A61K 31/353 424/438 |
|---|---|---|---|---|
| 9,694,042 | B1 * | 7/2017 | Terry | ................... A23K 20/158 |
| 2003/0175307 | A1 | 9/2003 | Gamer et al. | |
| 2005/0238731 | A1 | 10/2005 | Holt | |
| 2008/0038370 | A1 * | 2/2008 | Holt | ....................... A61K 31/07 424/643 |
| 2009/0252827 | A1 * | 10/2009 | Baginski | ................ A61K 36/48 426/2 |
| 2015/0104424 | A1 | 4/2015 | Scivoletto et al. | |

FOREIGN PATENT DOCUMENTS

| CN | 102688273 A | | 9/2012 |
|---|---|---|---|
| JP | 2003/137797 | * | 5/2003 |
| JP | 2003-137797 A | | 5/2003 |
| JP | 2003137797 A | | 5/2003 |
| KR | 10-2009-0131585 A | | 12/2009 |
| KR | 2009/0131585 | * | 12/2009 |

OTHER PUBLICATIONS

Gortzi O. et al. Study of Antioxidant and Antimicrobial Activity of Chios Mastic Gum Fractions . . . J of Food Processing and Technology 5(8)1-5, Aug. 2014. (Year: 2014).*
Int'l Search Report & Written Opinion (PCT/2017/034055), dated Aug. 16, 2017.
Advertisement for "Equine Intact Liquid", Intact Nutrition, retrieved from http://www.intactnutrition.com/view-product/equine-intact-liquid (Mar. 12, 2016).
Advertisement for "Starting Gate Nutritional Granules", SBS Equine—Shoe Bond Systems, Inc., retrieved from http://sbsequine.com/starting-gate-nutritional-granules/ (Mar. 9, 2016.
Advertisement for "Gastromax", retrieved from http://www.unitedvetequine.com/horse-digsetion/GastroMax3-horse-ulcer-prevention.asp (Mar. 4, 2016).
Advertisement for Gastro-Plex (Pellets), retrieved from https://www.smartpakequine.com/ps/gastroplex-pellets-13348 (Mar. 9, 2016).
"Equine Ulcer Medications & Gastric Health Supplements", retrieved from https://www.smartpakequine.com/equine-ulcer-medications-and-gastric-health-supplements-24pc.

(Continued)

*Primary Examiner* — Ralph J Gitomer
(74) *Attorney, Agent, or Firm* — Gregory L. Porter; Hunton Andrews Kurth LLP

(57) ABSTRACT

Embodiments of a method and supplement for preventing and/or treating gastrointestinal distress, including ulcer conditions, in animals are disclosed. The supplement comprises mastic gum and lecithin. The supplement may also comprise B vitamins, one or more prebiotics or probiotics, and one or more minerals as well as, pH buffers and flavoring. A disclosed method of preventing and/or treating gastrointestinal distress comprises orally dosing an animal with the supplement at least one daily.

20 Claims, 1 Drawing Sheet

(56) References Cited

OTHER PUBLICATIONS

"FDA Issues Warning Letters for Unapproved Omeprazole Drugs Marketed for Use in Ulcers", FDA, Center for Veterinary Medicine, retrieved from https://www.fda.gov/Animal/Veterinary/NewsEvents/CVMUpdates/ucm422694.htm (Mar. 4, 2016).

"Chios Mastiha Gum Resin for Equine Gastric Ulcers", retrieved from http://www.gravelproofhoof.org/#!mastiha=gum/ctjy (Mar. 12, 2016).

Advertisement for "Fantastic Mastic", Healing Bliss Botanicals, retrieved from http://www.healingbliss.ca/blogs/news/3852852-fantastic-mastic (Feb. 17, 2016).

"Equine Gastric Ulcer Syndrome", retrieved from http://www.scott-dunns.co.uk/equine_gastric_ulceration.htm (Feb. 17, 2016).

Advertisement—"Your Horse Ulcer-Free Pt. 3—Colonic Ulcers in the Hindgut", retrieved from http://www.succeed-equine.com/succeed-blog/2010/11/18/your-horse-ulcer-free-pt-3-colo (Aug. 28, 2014).

Advertisement—"Your Horse Ulcer-Free Pt. 5—Equine Ulcer Treatments", retrieved from http://www.succeed-equine.com/succeed-blog/2010/11/18/your-horse-ulcer-free-pt-5-equi (Aug. 28, 2014).

Advertisement—"Your Horse Ulcer-Free Pt. 6—Preventing Equine Ulcers", retrieved from http://www.succeed-equine.com/succeed-blog/2010/03/03/your-horse-ulcer-free-pt-6-prev (Aug. 28, 2014).

Publication—"EndurExtra High Fat for Horses—25 Lbs", Kentucky Performance (Feb. 2, 2012).

"Gastric Ulcers", retrieved from http://www.equisearch.com.article.eqhorseulc217 (Aug. 28, 2014).

"Chios Mastiha Gum Resin for Equine Gastric Ulcers", retrieved from http://www.gravelproofhoof.org/ (Dec. 29, 2014).

Excerpt of article—"Is Chios Mastic Used by Humans?", retrieved from http://imtelligenthorsecare.co.uk/product/chios-mastic-resin (Dec. 29, 2014).

"Chios Mastiha Gum Resin for Equine Gastric Ulcers", rertrieved from http://www.gravelproofhoof.org/ (Dec. 22, 2014).

"Ulcers: Is Mastic Gum the Breakthrough in Ulcer Treatment?", retrieved from http://www.health4youonline.com/PBCPPlayer.asp?ID=1342521 (Aug. 22, 2014).

Advertisement—Mastic Gum Mastic Gum Resin, retrieved from http://www.calmhealthyhorses.com/product_nz/masticgum.html (Dec. 29, 2014).

"Does mastic gum cure H.Pylori", retrieved form https://answers.yahoo.com/question/Index?qid-20060803111334bxFTm 08/06/20014.

"Mastic Gum Kills Helicobacter pylori", retrieved from http://www.nejm.org/doi/full/10/1056/NEJM1998/12243392618.

"Peptic Ulcers can be easily and quickly treated with antibiotics?", retrieved from http://hsionline.com/2009/06/15/mastic-gum/ (Aug. 5, 2016).

"Diagnosing and Treating Gastric Ulcers in Horses", CEH Horse Report, School of Veterinary Medicine, Univ.Cal. Davis (Oct. 2012).

Advertisement—"Natural Treatment for Gastric Ulcers in Horses", retrieved from http://sbsequine.com/natural-treatment-for-gastric-ulcers-in-horses (Apr. 7, 2014).

"Mastic", retrieved from http://www.drugs.com/npp/mastic.html (Nov. 5, 2015).

"AEC : Ulcergard v. Gastrogard—Which one do I use?", retrieved from http;//www.atlantaequine.com/pages/ulcergard_gastrogard.html.

Merial Labeling Information—Gastrogard (omeprazole) Oral Paste for Equine Ulcers (2000).

Advertisement—"Your Horse Ulcer-Free Pt. 2—Equine Gastric Ulcers", retrieved from http://www.succeed-equine.com/succeed-blog/2010/11/18/your-horse-ulcer-free-pt-2-equi (Aug. 28, 2014).

Gortzi et al., "Study of Antioxidant abd Antimicrobial Activity of Chios Mastic Gum Fractions Before and After Encapsulation in Liposomes", 5(8) J. Food Proc & Tech (2014).

Shakalis, "Equine Gastric Ulcers: A Real Problem with a Natural Solution", sbsequine.com Lec D-56 Mar. 2002.

\* cited by examiner

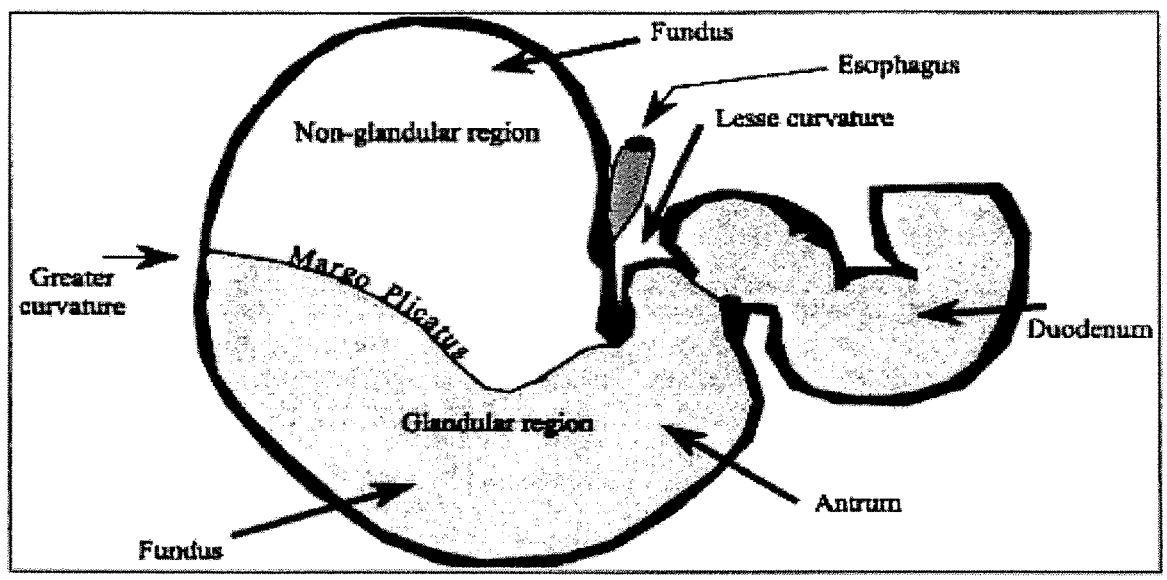
Equine stomach diagram

METHOD FOR THE PREVENTION AND TREATMENT OF GASTROINTESTINAL DISTRESS IN HORSES AND OTHER SPECIES

CROSS-REFERENCE TO RELATED APPLICATIONS

The instant application is a divisional of U.S. Ser. No. 15/161,689 filed May 23, 2016.

FIELD

Embodiments described herein are related to a nutritional supplement for the treatment and/or prevention of gastrointestinal distress in horses and other species of animals.

BACKGROUND AND SUMMARY OF THE INVENTION

The horse is a roaming animal with a gastro intestinal digestive system designed for and accustomed to grazing up to 17 hours a day. Thus, the horse's digestive system is specifically designed for the intake of small quantities of feed over long periods of time. Horses and certain other animals did not evolve to develop the mechanism which turns stomach acid on and off, like humans. Therefore, a horse's stomach typically produces stomach acid 24 hours a day even when there is no food present and such production can be up to 9 gallons of acidic fluid per day.

Stalled horses, with minimal access to pasture for grazing, are normally fed 2-3 times per day which leads to the buildup of excess stomach acid, as the stomach is subjected to prolonged periods of time without feed present to neutralize the acid. As such, gastric ulcers are quite common in domesticated/stalled horses and foals; their prevalence has been estimated at from about 50% to about 90%, depending upon the population surveyed and type and level of athletic activity in which the horses are engaged.

Foals are often subject to stomach ulcers causing morbidity and mortality. Clinical signs of ulcers in foals include intermittent colic (after suckling or eating), frequent recumbency (this is common in foals since this position seems to provide some relief from severe gastric ulceration), intermittent nursing, diarrhea, poor appetite, grinding of teeth and excessive salivation.

Adult horses with stomach ulcers may exhibit one or more clinical signs of ulcers including: poor appetite, attitude changes, decreased performance, reluctance to train or work, excessive recumbency, poor body condition, rough hair coat, weight loss, low grade colic and/or loose feces. More serious cases will show abdominal pain (colic) and/or grinding of the teeth. Others may walk away from food for a period of time as if the horse experiences discomfort when the food first contacts the stomach. Due to the range of common clinical signs of ulcers (and the fact that some horses with ulcers show no outward signs), the only clinically proven way to diagnose and verify stomach ulcers in horses is through gastric endoscopy or gastroscopy. Unfortunately, this involves placing an endoscope into the horse's stomach to examine its inner surface. This is unpleasant for the horse and sometimes a complex procedure for the veterinarian as it invariably requires anesthesia. In addition, this process can be very costly for the horse owner and a large number of veterinarians do not have access to an endoscope; due to the high cost basis for this type of equipment.

Unfortunately, currently available solutions for the prevention or treatment of ulcers or other gastrointestinal distress require a licensed caregiver to prescribe an oral administration of expensive treatments with a dosing syringe. In addition to being costly, many horses or other animals fight this type of treatment, which makes administration difficult.

What is needed is a method and supplement for prevention and/or treatment of gastrointestinal distress, including ulcer conditions in horses and other animal species. It would be further advantageous if the method and supplement employed generally available materials, which were safe and effective. It would be further advantageous if the supplement could be provided in a variety of forms and could be readily formulated with existing equipment. Advantageously, the present invention accomplishes one or more up to all of the aforementioned needs.

In one embodiment, the present invention relates to a nutritional supplement for the prevention or treatment of gastrointestinal distress in animals comprising mastic gum and lecithin. The supplement may alternatively be used to support a healthy digestive tract in a broad range of animals. In another embodiment, the present invention relates to a method of preventing gastrointestinal distress in an animal comprising: dosing an animal orally at least once daily with a supplement. The supplement comprises: mastic gum and lecithin in a weight ratio of mastic gum to lecithin of from about 1:10 to about 1:50 based on the total weight of mastic gum and lecithin. In another embodiment, the invention pertains to a method of preventing or treating ulcer conditions in a horse. The method comprises providing an effective amount of a supplement to address and/or treat gastrointestinal distress. The supplement comprises mastic gum, lecithin, one or more B vitamins, and one or more biotics selected from prebiotics, probiotics, and combinations thereof.

BRIEF DESCRIPTION OF THE DRAWINGS

FIG. 1 is a diagram of the typical equine stomach.

DETAILED DESCRIPTION

The present invention pertains generally to a nutritional supplement for the prevention or treatment of gastrointestinal distress in animals. It also pertains generally to a method of preventing gastrointestinal distress in an animal and more specifically to a method of preventing or treating ulcer conditions in a horse using a nutritional supplement as described herein.

As used herein "gastrointestinal distress" generally refers to gastrointestinal upset, ulcers, and other digestive conditions or disorders such as diarrhea that are suffered by non-human animals such as a horse, dog, sheep, alpaca, llama, camel, cat, donkey, and cow. In a preferred embodiment, the animal is a horse. The supplements and method described herein may be useful to prevent gastrointestinal distress and/or treat gastrointestinal distress in various animals including pigs, primates, guinea pigs, ferrets, elephants, marine mammals, rabbits, rats, dolphins, tigers, cheetahs, lions zebras, zoo animals, livestock, and domestic animals. Generally, the amount of supplement and/or dosage is higher when the supplements and/or methods are employed to treat as opposed to prevent distress. In certain instances and dosages, the supplements and/or methods may simultaneously treat and prevent further gastrointestinal distress.

FIG. 1 shows the typical equine digestive tract focusing on the stomach. The equine digestive process can be conceptually divided into the functions carried out in the front of the gastrointestinal tract and those carried out in the back of the GI tract. The functions carried out in the two areas can be very different. In the foregut, after food is gathered up, chewed, and swallowed, the stomach kicks into gear. The main functions of the stomach are to add gastric acid to help with the breakdown of food, to secrete the enzyme pepsinogen to begin protein digestion, and to regulate the passage of food into the small intestine. The stomach can be thought of as a holding and mixing tank, similar to a cement truck that is constantly churning and mixing ingredients.

While food breakdown may begin in the stomach, it continues in the small intestine, where secretions help with the further digestion of protein, simple carbohydrates, and fat. The small intestine is also the main site of nutrient absorption once the food is in small enough form. Amino acids, glucose, vitamins, minerals, and fatty acids are taken into the body as they move along the small intestine, so progress shouldn't be too fast or too slow.

The processes that occur in the hindgut, and particularly in the cecum and colon, are less about breaking down food into smaller, absorbable particles with the aid of enzymes and more about fermenting complex carbohydrates (fiber) into useful end products with the assistance of beneficial organisms. In addition to generating fatty acids, which supply energy or calories, these helpful microorganisms also produce B-vitamins, Vitamin K, and some amino acids. The colon then serves not only to absorb these nutrients but also a portion of the water that accompanies food as it moves along the digestive tract.

Mastic Gum and Lecithin Employed

The nutritional supplement generally comprises a mixture of mastic gum and lecithin. The types and amounts of mastic gum employed may vary. That is, the specific properties and amounts of the mastic gum that may be employed herein, of course may vary depending upon a number of factors including, for example, the desired results, the animal being treated as well as the types and amounts of other ingredients employed.

The mastic gum may be produced synthetically or, alternatively and more preferably, readily obtained from common natural sources. Mastic gum is sometimes known also as Chios Mastiha. Mastic gum is a natural resin that typically comes from an evergreen small tree or large shrub, which may be cultivated successfully in, for example, the Mediterranean such as the island of Chios, in the Eastern Aegean Sea. This evergreen tree called Schinos, belongs to the family of Pistachia. (Botanical name: Pistachia Lentiscus var. Chia). Mastic gum useful in the present invention is available commercially from sources such as Parchem or other chemical or nutritional supplement suppliers.

Generally, lecithin is a naturally occurring fatty substance or phospholipid, which could potentially be produced synthetically if desired. Lecithin may come from many sources, including both plant and animal tissues. Soybeans are the most common source of lecithin, but other potential sources of lecithin include: eggs, animal tissues, milk, fish eggs, rapeseed, cotton seed and sunflower.

A chemical formula for a lecithin is $C_8H_{17}O_5NRR'$ wherein R and R' are the same or different fatty acid groups. Pure lecithin is generally a phosphatidyl choline. That is, lecithins are mixtures of diglycerides of fatty acids linked to the choline ester of phosphoric acid. Thus, lecithins are often classed as phosphoglycerides or phosphatides (phospholipids). Commercially available lecithin is often a mixture of acetone insoluble phosphatides. For example, LECITHIN FCC, available from, for example, Spectrum Chemical, is a substance that is of a fatty nature and occurs naturally in animals and plant tissues. It is a brownish yellow color and contains a range of substances such as triglycerides, glycerol, phosphoric acid and so on. Other potential sources of lecithin useful in the present invention include, for example, Cargill.

The specific lecithin and amounts employed in the supplements and method of treatment/prevention also vary depending upon a number of factors. Such factors include, for example, the desired results, the animal being treated as well as the types and amounts of other ingredients employed and the form of the supplement. So long as the lecithin is capable of being mixed with the mastic gum, it may be in any form. Preferably, the lecithin employed may be in a form such as granules, powders, or even liquid such that it may be substantially homogeneously mixed with the mastic gum.

While not wishing to be bound to any particular theory, it is believed that feeding a lecithin with mastic gum aids in protecting gastric tissue from ulcer injury in, for example, horses and other animals in two ways. First, one or both ingredients may facilitate forming a barrier between stomach contents and epithelial cells, and second, one or both ingredients may facilitate cell membrane turnover and wound resealing.

Weight Ratios and Amounts of Mastic Gum and Lecithin Employed

As described previously, the amounts of mastic gum and lecithin employed vary depending upon a number of factors including, for example, the degree or severity, if any, of gastrointestinal distress, desired results, the animal being treated as well as the types and amounts of other ingredients employed and the form of the supplement. Other factors may include, for example, the activity level and/or diet of the animal.

Generally, the weight ratio of mastic gum to lecithin is determined such that the weight ratio is effective to prevent and/or treat gastrointestinal distress in an animal by providing the animal with about one to two or three or even four supplements per day. In such cases, the weight ratio of mastic gum to lecithin is a range from about 1:2500 to about 1:1.25, or from about 1:1000 to about 1:300, or from about 1:500 to about 1:100, or from about 1:10 to about 1:50 based on the total weight of mastic gum and lecithin. In other embodiments, the ratio of mastic gum to lecithin is a range from about 1:1 to about 1:100, or from about 1:10 to about 1:50, or from about 1:20 to about 1:40, or is a range from about 1:15 to about 1:35, or from about 0.5:40 to about 1.5:20.

Some embodiments may comprise the step of identifying an animal with ulcer conditions for treatment. A preferred embodiment also comprises the step of dosing an animal with the supplement for at least thirty days.

Supplement Form and Process of Making

The nutritionally supplement comprising lecithin, mastic gum and/or other ingredients is typically administered or provided orally to the animal in any convenient manner. The supplement may be formulated as a powder, paste, granule, liquid, gel, capsule, tablet or pellets. Various additives may be added to the supplement in order to achieve the desired physical form. In one embodiment, the supplement may be administered or provided as a top dressing on top of food at one or more regular daily feeding times.

The specific process of making the supplement, of course, will vary depending upon the final form desired, the specific ingredients and their form, amounts employed, and other factors. Generally, the process typically involves mixing the desired lecithin and mastic gum at ambient conditions to form a substantially homogenous mixture. If other ingredients are desired in the supplement, then in most cases the ingredients may be mixed prior to, simultaneously or even after the lecithin and mastic gum are mixed. In some cases, it may be desirable to add the desired amounts of lecithin and mastic gum to an already commercially available supplement lacking sufficient amounts of lecithin and mastic gum. Once the desired ingredients are mixed, they may be put in the desired form, e.g., powder, paste, granule, liquid, gel, or pellets using techniques known to those skilled in the art.

Other Ingredients

Other ingredients may be added to the supplement so long as the ingredients do not substantially interfere with the desired effects of the supplement comprising mastic gum and lecithin. In certain embodiments, the supplement may additionally comprise beneficial amounts of biotics such as probiotics and/or prebiotics, vitamins, minerals, and/or other nutritional supplements.

Probiotics are live "good" microorganisms, such as bacteria and yeast. Probiotics that may be useful in the supplement, particularly for equine supplements, include *Enterococcus faecium, Lactobacillus acidophilus, Lactobacillus caseii* and *Lactobacillus plantarum*.

Additional potential probiotics may include:

*Lactobacillus* species including, but not limited to, *L. rhamnosus, L. salivarius, L. paracasei, L. gasseri, L. reuteri, L. bulgaricus, L. brevis, L. brevis, L fermentum*, and *L. reuteri*.

*Bifidobacterium* species including, but not limited to, *B. bifidum, B. longum, B. infantis, B. breve,* and *B. lactis*.

*Bacillus* species including, but not limited to, *B. coagulans* and *B. subtillius*.

*Streptoccocus* species including, but not limited to, *S. salivarius, S. thermophilus, S. cremoris, S. faecium* and *S. infantis*.

Other useful species may include, but are not limited to, *Saccharomyces boulardii, Aspergillus oryzae, Saccharomyces cerevisiae*, and *Aspergillus niger.*

The amount of probiotic to include in the supplement varies depending upon, among other items, the type of probiotic, other ingredients, and desired results. Typically, an amount of probiotic is measured in colony forming units (CFU's) per dose. In many cases, from millions to even billions of CFUs of probiotic may be included in a given supplement. Typically, the amount of probiotic may be at least 500 million, preferably at least 1 billion, more preferably at least 2 billion, preferably at least 3 billion up to as much as 10 billion CFUs per dose of supplement. Certain embodiment may comprise at least 10 to 15 billion CFUS per dose of supplement.

Disclosed embodiments may comprise at least 500 million, preferably at least 1 billion, more preferably at least 2 billion, preferably at least 3 billion up to as much as 10 billion CFUs of each species of *Lactobacillus acidophilus, Lactobacillus plantarum, Lactobacillus casei*, and/or *Enterococcus faecium* per dose of supplement.

In contrast to probiotics, prebiotics are the foods that feed the probiotics. Examples of prebiotic that may be included, particularly in equine supplements, include fructooligosaccharides (FOS), xylooligosaccrarides (XOS), polydextrose, pectin and psyllium. Additional potential prebiotics include the following:

Larch arabinogalactin (LAG), resistant starch, beta-glucans, trans-galactooligosaccharide, inulin, oligofructose, gum arabic, chicory root, Jerusalem artichoke, dandelion greens, garlic, leek, onion, asparagus, wheat bran, wheat flour, and banana.

Prebiotics may include short-chain prebiotic with 2-8 links per saccharide molecule or longer-chain prebiotics with 9-64 links per saccharide molecule. Prebiotics may comprise any of the above in combination as in Oligofructose-Enriched Inulin (OEI).

Prebiotic food ingredients are generally not digested by horses or other animals. Instead, prebiotics are digested by desirable microorganisms and probiotics in the digestive system to increase or enhance the numbers and/or activity of the desirable microorganisms and/or probiotics. Thus, including both probiotics and prebiotics in the supplement may assist in further treating or preventing GI-related concerns, such as diarrhea, by facilitating the growth of the good microbes and/or minimizing the invasion and growth of disease-causing bacteria. Probiotics and/or prebiotics may be particularly preferable in supplements employed in animals such as horses that are on antibiotics or experiencing stress, transport, abrupt dietary changes, and/or Clostridium or Salmonella infections. Any of these may potentially alter the normal microbe population in, for example, a horse's large intestine.

If prebiotics are to be employed in the supplement, then the amount may vary widely depending upon, among other items, the type of prebiotic, other ingredients, and desired results. Typically, an amount of prebiotic is at least about 0.01, or at least about 0.1, or at least about 0.4 up to about 1, or up to about 2 grams per dose.

In addition to mastic gum, lecithin, probiotics and prebiotics, a wide variety of vitamins, minerals, or other nutritional supplements may be included in the described nutritional supplement. Such other ingredients include, for example, B vitamins such as, for example, Vitamin B1 (thiamine) A coenzyme in the catabolism of sugars and amino acids; Vitamin B2 (riboflavin) A precursor of cofactors called FAD and FMN, which are needed for flavoprotein enzyme reactions, including activation of other vitamins; Vitamin B3 (niacin or nicotinic acid) A precursor of coenzymes called NAD and NADP, which are needed in many metabolic processes; Vitamin B5 (pantothenic acid) A precursor of coenzyme A and therefore needed to metabolize many molecules; Vitamin B6 (pyridoxine, pyridoxal, pyridoxamine) A coenzyme in many enzymatic reactions in metabolism; Vitamin B7 (biotin) A coenzyme for carboxylase enzymes, needed for synthesis of fatty acids and in gluconeogenesis; Vitamin B8 (inositol); Vitamin B9 (folic acid) A precursor needed to make, repair, and methylate DNA; a cofactor in various reactions; especially important in aiding rapid cell division and growth, such as in infancy and pregnancy; Vitamin B12 (various cobalamins; commonly cyanocobalamin or methylcobalamin in vitamin supplements) A coenzyme involved in the metabolism of every cell of the human body, especially affecting DNA synthesis and regulation, but also fatty acid metabolism and amino acid metabolism.

For certain embodiments, the ratio of total B-vitamins to mastic gum is from about 1:0.1 to about 1:4, or from about 1:0.3 to about 1:2, or from about 1:0.6 to about 1:1. B-vitamins may refer to all known B-vitamins including: thiamine, riboflavin, niacin, nicotinic acid, pantothenic acid, pyridoxine, pyridoxal, pyridoxamine, biotin, folic acid, folinic acid, cyanocobalamin, methylcobalamin or other cobalamins, choline, adenine, or carnitine, adenosine monophosphate (AMP), inositol, para-aminobenzoic acid, pterylhepta-glutamic acid, orotic acid, dimethylglycine, L-carnitine, carnitine, and myo-inositol.

Other useful ingredients for the supplement may include DL methionine, Vitamin E, zinc, selenium, distillers dried grains with or without solubles, magnesium mica, corn distillers dried grains, wheat middlings, alfalfa meal, dehydrated alfalfa, rice mill by product, rye flour, beet pulp, dicalcium phosphate, flaxseed meal, oat flour, oat oil, magnesium stearate, cellulose, silicon dioxide, gelatin, maltodextrin, silica, fructose, inulin, inouline, soy protein isolate, rice bran, soybean flour, coconut meal, marine lipid concentrates, kelp, kaolin, and/or pectin.

If desired, formulation aids and/or flavoring aids may be employed in the supplement at useful amounts. Such ingredients include, for example, silicon dioxide, maltodextrin, vanilla flavor, and the like. Some embodiments may contain a pH buffer or alkalinizing agent. Alternative embodiments may contain an additive for coating the interior of an animal stomach. Still other embodiments may contain anti-fungal additives.

Chart 1 below shows a potential embodiment as well as potential dosage ranges for the disclosed supplement. Such a supplement would be particularly preferable for horses at a dose of about once daily for preventing gastrointestinal distress. If desired, the supplement could be administered in two or even three or more daily doses for treatment purposes depending upon the severity of the distress. In certain circumstances administering a dose every other day, every third day, or weekly may be appropriate depending on the nature and severity of the distress. Generally, each of the below ingredients with the exception of mastic gum and lecithin are optional and thus need not be present at even the low level described in Chart 1 below. That said, it is often preferable to include at least the prebiotics and probiotics with the mastic gum and lecithin.

CHART 1

| | | Dose Amount Range | |
|---|---|---|---|
| | Formulation | Low | High |
| Mastic Gum | 1.00 gm | 0.02 gm | 4.00 gm |
| DL Methionine | 1.72 gm | 0.05 gm | 3.00 gm |
| Inositol | 368 mg | 100 mg | 550 mg |
| Niacin | 135 mg | 10 mg | 250 mg |
| Thiamine | 42 mg | 10 mg | 150 mg |
| Riboflavin | 38 mg | 10 mg | 75 mg |
| Pyridoxine | 20 mg | 5 mg | 30 mg |
| Biotin | 2 mg | 0.2 mg | 20 mg |
| Vitamin B12 | 184 mcg | 50 mcg | 500 mcg |
| Vitamin E | 123 mg | 30 mg | 250 mg |
| Zinc | 1% | 0.03% | 2% |
| Selenium | 40 ppm | 10 ppm | 100 ppm |
| FOS - Prebiotics | 0.5 gm | 0.01 gm | 2.0 gm |
| Soy Lecithin | 28.7 gm | 5.0 gm | 200 gm |
| | | | (preferably up to 50 gm) |
| Probiotics | 3 billion CFU's | 500 million CFU's | 10 billion CFU's |
| *Lactobacillus acidophilus, Lactobacillus plantarum, Lactobacillus casei, Enterococcus faecium* | | | |
| Silicon Dioxide | 1% | .05% | 2% |
| Maltodextrin | 2.8% | 1% | 5% |

Example Study Using the Formulation in Chart 1 Above in Quarter Horses

Eight quarter horses, which were actively engaged in racing or race training, were examined. These horses were positively diagnosed with significant and differing levels of Equine Gastric Ulcer Syndrome (EGUS), gastric erosions or lesions in the stomach. The gastric ulcers or lesions were verified through endoscopies on all horses in the initial phase of the study. Inclusion criteria were horses specifically showing significant gastric ulceration and between the ages of 2-6 years. The significant gastric ulceration was confirmed by gastro scope and clinical observation. All horses selected were quarter horses in heavy training, most were young horses in race training.

The horses were all stalled and no changes in management occurred in the study time frame to confuse or affect the results of the study (i.e. horses removed from training, turned out to pasture or diet changes). These horses were all fed free choice Bermuda hay with a 14% sweet feed or Strategy as a grain source three times per day at three pounds each feeding. Additional supplementation included powder form electrolytes. None of the horses received any drug therapy thirty (30) days prior to start of the study or during the study.

Three horses were randomly selected to receive the supplement 3× per day (horse #5, #6 and #7). Five horses were randomly selected to receive the supplement 2× per day (horse #1, #2, #3, #4 and #8). The supplement provided was in a one (1) ounce dose as in Chart 1 above (reproduced below).

| Supplement given 3× per day or 2× per day | |
|---|---|
| Mastic Gum | 1.00 gm |
| DL Methionine | 1.72 gm |
| Inositol | 368 mg |
| Niacin | 135 mg |
| Thiamine | 42 mg |
| Riboflavin | 38 mg |
| Pyridoxine | 20 mg |
| Biotin | 2 mg |
| Vitamin B12 | 184 mcg |
| Vitamin E | 123 mg |
| Zinc | 1% |
| Selenium | 40 ppm |
| FOS - Prebiotics | 0.5 gm |
| Soy Lecithin | 28.7 gm |
| Probiotics | 3 billion CFU's |
| *Lactobacillus acidophilus, Lactobacillus plantarum, Lactobacillus casei, Enterococcus faecium* | |
| Silicon Dioxide | 1% |
| Maltodextrin | 2.8% |

After ten days of product supplementation, urine samples were collected from each horse and sent to an outside independent laboratory for testing. After a minimum of thirty (30) days, all horses were examined and endoscopies performed to evaluate product results.

All horses in the study showed good acceptance of the product, no side effects were reported and all horses tested negative for NSAIDS (non-steroidal anti-inflammatory drugs), Fluphenazine, Fluoetine and Reserpine. After thirty (30) days of supplementation, all horses, except one, showed significant improvement after the 2× or 3× daily supplements. The one horse that did not show improvement (Horse #8) was ultimately removed from the study due to the severity of the initial and ongoing ulcerations and need for comprehensive treatment. For the remaining seven horses, improvement was observed, positively verified and documented through endoscopies performed on all horses.

In less than 60 days on the product, Horse #7 had numerous Grade II and Grade III ulcers reduced to Grade I Ulcer and Hyperkeratosis. Horse #5 was diagnosed with Grade I and Grade II ulcers on 70% of the stomach wall. In less than 60 days on the product, this condition improved to Grade I ulcers and diffuse hyperkeratosis. Horse #7 initially showed numerous Grade II and Grade III ulcers and in a time period of just 30-60 days on the product, these ulcers were ultimately reduced to Grade I Ulcer and Hyperkeratosis. Horse #5 was initially diagnosed with Grade I and Grade II ulcers on 70% of the stomach wall. In only 30-60 days on the product, this condition improved and ultimately reduced to Grade I ulcers and diffuse hyperkeratosis.

Table 1 below shows the detailed assessments of the individual horses based on the initial gastroscope (positively diagnosing the severe ulceration) and the follow-up gastroscope documenting the results after product supplementation for 30-60 days.

TABLE 1

| HORSE | DAY 1 | DAY 30 - 60 |
|---|---|---|
| #1<br>4 yr. old QH<br>stallion | Blister formation<br>Hyperkeratosis<br>Multiple Grade I ulcers | Hyperkeratosis<br>Grade I ulcers<br>on greater<br>curvature of<br>the stomach |

TABLE 1-continued

| HORSE | DAY 1 | DAY 30 - 60 |
|---|---|---|
| #2<br>6 yr old QH<br>gelding | Hyperkeratosis<br>Grade II ulcers | Hyperkeratosis<br>has improved<br>Grade II ulcers<br>remain |
| #3<br>2 yr. old QH<br>gelding | Hyperkeratosis | Hyperkeratosis<br>improved |
| #4<br>2 yr. old QH<br>gelding | Grade I ulcers | Grade III<br>ulceration present |

TABLE 1-continued

| HORSE | DAY 1 | DAY 30 - 60 |
|---|---|---|
| #5 2 yr. old QH filly | Grade I and Grade II ulcers on 70% of stomach wall | Grade I ulcers, small in diameter Diffuse Hyperkeratosis |
| #6 3 yr. old QH gelding | Grade II and Grade III ulcers on lesser curvature of the stomach Greater curvature conctration and margo plicatis | Grade II and Grade III ulcers on margo plicatis Hyperkeratosis on greater curvature of the stomach |
| #7 2 yr. old QH gelding | Grade II and Grade III ulcers on greater curvature of the stomach | 1 - Grade I ulcer Hyperkeratosis Multiple superficial erosions |
| #8 2 yr old QH gelding | Hyperkeratosis on lesser curvature Grade II ulcers on 50% of greater curvature of the stomach | Marked Hyperkeratosis Grade I and Grade II ulcers on margo plicatis |

*horse #8 was ultimately removed from the study due to the severity of initial and ongoing ulcerations.
Placed under care for comprehensive treatment.

The results of this study show the positive effects of utilizing this product in horses with severe gastric ulcers or lesions.

Terms and Definitions Used in the Example Study Above

| Ulceration/Lesion Grading Scale: | |
|---|---|
| 0 | Normal |
| Grade I | Intact Mucosa with reddening or hyperkeratosis |
| Grade II | Mild ulceration—small single or multifocal lesions, mild hyperkeratosis |
| Grade III | Moderate ulceration—large single or extensive multifocal lesions |
| Grade IV | Severe ulceration—extensive lesions with areas of deep ulceration |

Hyperkeratosis- term often used in connection with lesions of the mucous membranes.
Margo Plicatus- cuticular ridge that separates the squamous mucosa from the glandular mucosa, in the equine stomach.
Recumbency- lying back or lying down, resting or leaning against something else.

Ulcer conditions should be understood to include various levels of Equine Gastric Ulcer Syndrome, gastric erosions, lesions in the stomach or other area of the digestive system in horses and other species.

The terms, descriptions and examples used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A method of preventing or treating gastrointestinal distress in an equine animal comprising:
    dosing the equine animal orally at least once daily with a supplement, said supplement comprising:
    mastic gum; and
    lecithin;
    wherein the supplement comprises from about 0.02 to about 4 grams mastic gum; and from about 5 to about 50 grams lecithin.

2. The method of claim 1, wherein said animal is a horse.

3. The method of claim 1, wherein the dosing comprises providing the supplement as a top dress at a regular feeding.

4. The method of claim 1, wherein the equine animal is dosed with the supplement at least two times per day.

5. The method of claim 1, wherein the lecithin comprises soy lecithin.

6. The method of claim 1, wherein the supplement further comprises one or more B-vitamins, one or more minerals, or a combination thereof.

7. The method of claim 6, wherein the weight ratio of the one or more B-vitamins to mastic gum is from about 1:0.1 to about 1:4 based on the total weight of B-vitamins and mastic gum.

8. The method of claim 1, wherein the supplement is in the form of a pellet, powder, granule, liquid, or gel.

9. The method of claim 1, wherein the supplement further comprises one or more prebiotics, one or more probiotics, or a combination thereof.

10. The method of claim 1, wherein the supplement further comprises a pH buffer.

11. The method of claim 1, wherein the supplement further comprises one or more B-vitamins, one or more minerals, one or more prebiotics, and one or more probiotics.

12. A method of preventing or treating ulcer conditions in a horse comprising:
    dosing the horse with an effective amount of a supplement comprising mastic gum and lecithin wherein the weight ratio of mastic gum to lecithin is from about 1:10 to about 1:50 based on the total weight of mastic gum and lecithin.

13. A method of preventing or treating ulcer conditions in a horse comprising:
    dosing the horse with an effective amount of a supplement, wherein the supplement is provided to the horse from one to three times daily and wherein the supplement comprises from about 0.5 to about 1.5 grams of mastic gum and from about 10 to about 40 grams of soy lecithin.

14. The method of claim 13 wherein the supplement further comprises from about 500 million to about 10 billion CFUs of one or more probiotics selected from the group consisting of *Enterococcus faecium, Lactobacillus acidophilus, Lactobacillus caseii, Lactobacillus plantarum*, and mixtures thereof.

15. The method of claim 13 wherein the supplement is provided to the horse in the form of top dressing for at least about 30 days.

16. The method of claim 13, wherein the lecithin comprises soy lecithin.

17. The method of claim 13, wherein the supplement is in the form of a powder.

18. The method of claim 13, wherein the supplement further comprises one or more B-vitamins, one or more minerals, or a combination thereof.

19. The method of claim 13, wherein the supplement further comprises one or more B-vitamins wherein the weight ratio of the one or more B-vitamins to mastic gum is from about 1:0.1 to about 1:4 based on the total weight of B-vitamins and mastic gum.

20. The method of claim 13, wherein the supplement is provided to the horse from one to three times daily and wherein the supplement comprises from about 0.5 to about 1.5 grams of mastic gum, from about 10 to about 40 grams of soy lecithin, and one or more prebiotics or probiotics.

* * * * *